United States Patent [19]

Secher et al.

[11] 4,423,147

[45] Dec. 27, 1983

[54] MONOCLONAL ANTIBODY TO INTERFERON-α

[76] Inventors: David S. Secher, 2 Nightingale Ave., Cambridge, England, CB1 4SQ; Derek C. Burke, 41 Portland St., Leamington Spa, Warwickshire, England, CV32 5EY

[21] Appl. No.: 333,856

[22] PCT Filed: Apr. 13, 1981

[86] PCT No.: PCT/GB81/00067
§ 371 Date: Dec. 10, 1981
§ 102(e) Date: Dec. 10, 1981

[87] PCT Pub. No.: WO81/02899
PCT Pub. Date: Oct. 15, 1981

[30] Foreign Application Priority Data
Apr. 11, 1980 [GB] United Kingdom ............... 8012096

[51] Int. Cl.³ .................... G01N 33/54; G01N 33/68; C12Q 1/00
[52] U.S. Cl. ......................................... 435/68; 435/7; 435/172; 435/811; 436/518; 436/536; 436/178; 436/815; 436/824; 260/112.5 R
[58] Field of Search ............... 424/11.5; 436/548, 518, 436/177, 536, 178, 824, 815; 435/4, 7, 68, 172, 240, 811

[56] References Cited

U.S. PATENT DOCUMENTS 4,172,124 10/1979 Koprowski et al. ............... 424/85
4,196,265 4/1980 Koprowski et al. ............... 435/2

FOREIGN PATENT DOCUMENTS 2492842 4/1982 France ............... 435/172

OTHER PUBLICATIONS

Montagnier, L. et al., C. R. Acad. Sci. Paris, Series D. vol. 291 (11), pp. 893-896 (11/80).
Arnheiter, H. et al., Nature, vol. 294, pp. 278-280 (11/81).
Nature, vol. 285, pp. 446-450 (6/80) Secher, David S. and Burke, Derek C.
Nature, vol. 290, pp. 501-503 (4/81) Secher, D. S.
J. Immunology, vol. 128, pp. 2824-2825 (6/82), IMAI et al.
Proc. National Academy Sciences, vol. 78, pp. 1848, (1981) Staehelen, T. et al.
J. General Virology, vol. 53 (2), pp. 257-265 (1981) Morser et al.
Infection and Immunity, vol. 19 (2) pp. 570-574 (1978) Dalton, B. J. et al.
Olsson, J. et al., Proceedings National Academy Sciences, vol. 77, p. 5429 (1980).

Primary Examiner—Benjamin R. Padgett
Assistant Examiner—M. Moskowitz
Attorney, Agent, or Firm—Cushman, Darby & Cushman

[57] ABSTRACT

A monoclonal antibody is described characterized by its specificity to interferon-α (leukocyke interferon). Preferably the antibody has specificity to human interferon-α. The monoclonal antibody is secreted by a hybrid cell formed by the fusion of lymphocyte cells derived from an animal immunized with interferon-α, with mycloma cells. The antibody has applications in the purification of interferon. It may be covalently attached to a solid support and used as an immunoadsorbent. Purifications of up to 5000 fold may be obtained in a single pass through an immunoadsorption column of this type. An immunoradiometric assay for interferon-α is also described.

7 Claims, No Drawings

MONOCLONAL ANTIBODY TO INTERFERON-α

FIELD OF THE INVENTION

The present invention relates to a monoclonal antibody produced by a hybrid cell line characterised in that the antibody has specificity to interferon-α. The present invention also relates to the use of this monoclonal antibody in a process for the purification of interferon-α and in immunoassay of interferon-α.

BACKGROUND TO THE INVENTION

In recent years advances in theory and in research techniques have led to a better understanding of the manner in which the mammalian immune response system operates. It is now accepted that when antigens are introduced into the mammalian body, lymphocyte cells synthesise antibody molecules which have the property of binding to specific sites (determinants) on the antigens and rendering them innocuous. The deliberate stimulation of the immune response system is a common technique for the production of antisera, the applications of which are legion (e.g. in the production of vaccines, in pathology and in medical and zoological research).

One problem inherent in antisera produced in this way is the variation in physiological activity that they exhibit.

This effect may be attributed, at least partially, to the number of specific antibodies produced as a result of the stimulating immunization. In addition to the antibodies produced to antigenic impurities in the immunizing medium, each antigen to which an antibody is required may possess a plurity of determinant sites. Thus, the "cocktail" of antibodies produced by the body will be complex, its composition may be variable, synergistic effects may be evident and when administered to a different mammal, even within the same species its physiological effect is likely to be different as a result of differences in the combination of determinants present in the donor mammal and in the recipient.

A further problem in the production of antisera in this way is the cost of extraction and purification which renders samples of clinical purity expensive.

Research in the field of molecular biology has now provided an alternative source if antibodies. It has been discovered that fusion between lympocyte cells and myeloma cells derived from mammals (e.g. mice and rats) can produce hybrid cells capable of replication in vitro, (see Köhler and Milstein, Nature 256, 495–597). Such hybrid cells have the property of secreting an antibody of predefined specificity. This specifity is that of the antibody produced by the lympocyte involved in the fusion. The hybrid cells may be cloned and grown in stable culture to produce in the culture supernatant samples of antibody to a specific determinant. Antibodies produced in this way are known as monoclonal antibodies in the art.

The general method of production of hybrid cell lines of the type described above comprises the steps of immunizing a animal (usually a rat or mouse, but not necessarily one of these) with an antigen to which a monoclonal antibody is required. After allowing time for the immune system to generate lymphocytes secreting the antibodies to the antigen, the animal is sacrificed and a suspension of spleen cells is prepared. Fusion between these cells and myeloma cells is achieved by bringing them into contact in the presence of a fusion promoter (e.g. polyethyleneglycol). A small percentage of the cells fuse to produce hybrid myeloma cells. The immunization results in a plurality of different lymphocytes each secreting antibody to a different antigenic determinant, and these characteristics are transferred genetically to the hybrid cells. It is possible, by careful screening, to isolate from a culture of hybrid cells, a cell having the desired specificity. Such cells may be cloned and cultured.

The advantage at this technique is that it provides a source of a specific antibody uncontaminated by antibodies raised to other determinants either on the antigen with which the mammal was immunized or on antigenic impurities in the immunizing material. Another advantage of the technique is that antigen not available in a pure form for screening assays and present in the immunizing material at low concentrations, may be used.

Clearly the success of the process relies upon an efficient screening assay to be applied after the cell fusion stage.

The present invention concerns a monoclonal antibody to leukocyte interferon (also known in the art as interferon-α). This protein, or group of proteins (present evidence suggests about 15 distinct molecular entities) is currently the centre of considerable interest in the medical world following the discovery of its antitumour and antiviral activity. Interest amongst researchers worldwide has created a demand for substantial quantities of interferon to be used not only for clinical trials but also by research establishments attempting to produce a more detailed picture of the mammalian immune response system and the action of interferons therein. Considerable progress has been made in the characterisation of human (and mouse) interferons including amino acid compositions and aminoterminal sequences.

The size and nature of this demand necessitates large scale production including extensive purification stages, the complexity of which renders interferon prohibitively expensive for routine use.

Interferon is available from lymphoblastoid cells, from white blood cells (buffy coat lymphocytes), and from genetically modified bacteria. Improvements in purification techniques have recently allowed the purification of interferons to homogeneity. Two of the three species of interferon have been purified to this point, namely: fibroblast interferon (interferon β) and leukocyte interferon.

The monoclonal antibody the subject of the present invention may be used in purification process which results in a purity of interferon hitherto not available in substantial quantities.

SUMMARY OF THE INVENTION

According to the present invention there is provided a monoclonal antibody produced by a hybrid cell line characterised in that the antibody has specificity to interferon-α.

Preferred is a monoclonal antibody wherein the antibody has specificity to human interferon-α.

Further preferred is a monoclonal antibody wherein the antibody is an immunoglobulin molecule of the type IgG or IgM.

Further preferred is a monoclonal antibody produced by a cell hybrid wherein the cell hybrid is derived from tissue from an animal selected from the group consisting of mouse, rat, human, guinea pig and rabbit.

Further preferred is a monoclonal antibody when used in a process for purifying interferon-α.

Further preferred is a monoclonal antibody when used in an immunoadsorption purification process for interferon-α.

Further preferred is a monoclonal antibody when used in an immunoassay for interferon-α.

DETAILED DESCRIPTION OF THE EMBODIMENTS

The invention is described by the following experimental details which are given by way of example, not of limitation.

A general survey at the experiment is given, followed by a more detailed description of the methods employed.

Groups of mice and rats were immunized at 2-weekly intervals with lymphoblastoid interferon emulsified in complete Freund's adjuvant. A mouse with a titre (the dilution of serum that neutralized 50% of 20U interferon) of $\log_{10} 3.7$ was selected for the fusion. Details of the immunization and fusion, are given below.

Three cultures (3,5,13), among several showing possible anti-interferon activity, were recloned in soft agar as described and 48 clones of each were picked and grown in 2-ml cultures. Culture supernatants were tested for the presence of secreted mouse immunoglobulin using a reverse plaque assay (spot-test) and for anti-interferon activity in the INAS$_{50}$ assay(Atherton & Burke J.gen Virol 29 297-304(1975). The results as well as the results of many other assays clearly demonstrated that the level of neutralization of interferon by culture supernatants was just at (and sometimes beyond) the limits of sensitivity of the assay. At the critical stage of selection of a positive clone of NK2/13, the reverse plaque assay was essential.

To confirm that the anti-interferon activity was in fact due to immunoglobulin, and to determine the immunoglobulin class, $^{14}$C-lysine was incorporated into proteins secreted by selected clones and the extracellular medium analysed by SDS-polyacrylamide gel electrophoresis (PAGE) in reducing conditions. Only two major bands were visible in each case; one had the mobility of immunoglobulin heavy chain (γ,NK2/13.35; μ,NK2/13.36), the other co-migrated with the immunoglobulin light chain (NSI) that was run as a marker.

Clone NK2/13.35 was recloned and the most strongly positive subclone (NK2/13.35.6) in the neutralization assay was grown to mass culture and frozen in liquid nitrogen for long-term storage. This clone was also grown in the presence of $^{14}$C-lysine and the radioactive secreted proteins analysed by SDS-PAGE. Two major bands were visible; one had the mobility of immunoglobulin γ-chain, the other had a mobility slightly lower than that of the NSI light chain. No band corresponding to the NSI light chain was detectable, indicating that the clone NK2/13.35.6 produces only the antibodyspecific heavy and light chains.

The NK2/13.35.6 culture supernatant, although usually positive, was at best only sufficient to reduce the interferon activity to 25% of its control value using the interferon neutralization assay described further below. Some modifications to the assay were therefore tested. Concentration of culture supernatants 10-20 fold by ultrafiltration (Amicon XM 50) or by ammonium sulphate precipitation increased reproducibility, but the difference between a positive and a negative supernatant was not always convincing. However, the results did show that the anti-interferon activity was associated with a high molecular weight (MW) component which was precipitated by 50% saturated ammonium sulphate. We also looked for, but could not detect, a synergistic effect on mixing supernatants from different cultures. Such an effect might result from the mixing of two non-neutralizing monoclonal antibodies, neither of which alone would be detectable. A similar phenomenon has been observed in studies of monoclonal antibodies to cell-surface antigens. A more successful modification to the assay was the introduction of an indirect immunoprecipitation (IIP) step (see below) in which interferonanti-interferon complexes are removed (by the addition of carrier mouse immunoglobulin and anti-mouse immunoglobulin antiserum) before adding the interferon to the cells.

A purified IgG fraction prepared from the serum of mice bearing NK2 tumours was used to allow a higher concentration of immunoglobulin to be tested in the assay. (As the only clone from the NK2 fusion to be grown in mice was NK2/13.35.6 it will be abbreviated to NK2.) The separation of the antibody-antigen complex formation from the neutralization part of the assay allowed the use of much higher levels of interferon as the interferon was diluted for assay after removal of the antibody-antigen complex. This greatly increased the precision of the assay because, by varying the dilution of the sample for interferon assay, we could always work near the midpoint of the dose-response curve. This is impossible in the neutralization assay.

Using the IIP assay we found that at an antibody conconcentration of about 90 μg ml$^{-1}$ it was possible to remove over 90% [696/720 U (reference research units as defined relative to the MRC reference standard preparation 69/19)] of input interferon.

A detailed description of the methods employed now follows.

The interferon used as immunogen for the first series of mice inoculations was human lymphoblastoid interferon [HuIFN-α(Ly)]. This was produced in Namalwa cells by induction with Sendai virus after pretreatment with sodium butyrate. The interferon was then concentrated by precipitation with ammonium sulphate to yield a product which contained $2 \times 10^5$ reference research units/ml of interferon and had a specific activity of $5.3 \times 10^5$ reference research units/mg protein. This material was used as the immunogen for the first series of inoculations. The immunogen for the second series of mice inoculations was partially purified HuIFN-α(Ly). This material was prepared as described above and partially purified by immunochromatography. Two batches were used: the first, which was used for primary immunization contained $7.2 \times 10^6$ reference research units/ml and had a specific activity of $2.4 \times 10^7$ units/mg protein; the second, used for the final intravenous inoculation (602/10), contained $6.0 \times 10^6$ reference research units/ml, and had a specific activity of $9.3 \times 10^7$ units/mg protein.

One group of six Balb/c mice (female, 18 to 22 g) and a group of three rats were injected. The mice were injected once every 2 weeks intraperitoneally with about $3 \times 10^4$ units interferon in 0.16 ml (first series) or once a week with about $10^6$ units interferon in 0.16 ml (second series) emulsified in complete Freund's adjuvent, and then at 2-week intervals for up to 12 weeks with a similar dose of interferon in incomplete Freund's adjuvant. The rats were injected in the footpads (intradermally) and in the hind leg (intramuscularly) or in multiple subcutaneous sites. About $10^6$ units emulsified in complete Freund's adjuvant (total vol. 0.6 ml) was injected/rat at approx. 2-week intervals. The mice and rats were bled from the tail vein, in order to follow the production of antibodies against interferon, by incubating serial 0.5 $\log_{10}$ dilutions of the serum with 10 units lymphoblastoid interferon at 37° C. for 1 hour before assay of the residual interferon titre. The anti-interferon titre was defined as the reciprocal of that dilution of serum that reduced the interferon titre by 50%.

Interferon was routinely assayed by the inhibition of nucleic acid synthesis (INAS) method in which the effect of interferon pretreatment upon subsequent viral RNA synthesis is measured. The cells used for assay were bovine turbinate cells, cat lung cells, EBtr cells, several strains of human fibroblasts, L6/1 rat cells, L-929 mouse cells and Madin-Derby bovine kidney (MDBK) cells. On some experiments interferon was also assayed by reduction in cytopathic effect (c.p.e.), yield reduction or plaque reduction assays. All human interferon titres are quoted in reference research units using the HuIFN-α reference research standard 69/19.

Two groups of mice and one group of rats were immunized with two different preparations of lymphoblastoid interferon. Testing of the serum demonstrated that interferon was immunogenic in both species. In the rats, there appeared to be a primary and then a short secondary response. The level of antibody could not be boosted after a period of rest and no rat has been used for fusion. The response of the mice varied from one animal to another, but the titres generally increased until a plateau was reached, which was little affected by further immunization. Considerable variation in response was seen between different mice. No difference was seen in the anti-interferon titres produced when either crude or partially purified interferon was used as the immunogen.

Spleen cells from the mouse with the highest serum anti-interferon titre in each group were used for fusion.

These mice were injected intravenously with $1 \times 10^5$ units interferon (first series) or $2.2 \times 10^6$ units interferon (second series) and 4 days later the mouse was bled and the spleen removed for fusion with NSI myeloma cells. Following fusion, cells were grown in 48 2 ml cultures (24-well Linbro plates), and hybrid cells were selected and cloned as described. One to 3 weeks after the fusion, growth of hybrid cells was seen in all 48 wells, and the culture supernatants were assayed for anti-interferon activity.

Supernatant fluids from cell hybrids were assayed either directly for anti-interferon activity, or indirectly by an immunoprecipitation (IIP) procedure. In the direct procedure, supernatant fluids (0.5 ml) were mixed with an equal volume of Dulbecco's modified Eagle's medium (DMEM). 20% foetal calf serum (Gibco-Biocult) containing about 2 units HuIFN-α(Ly). After incubation at 37° C. for 1 h, the fluids were assayed for residual interferon by the INAS assay in HFF cells, using $2 \times 0.5$ ml vol. for duplicate cultures in small glass vials (1 cm diam). This dose of interferon produces a 50% depression of virus RNA synthesis; i.e. 1 HFF interferon unit is equivalent to 2 reference research units. When other cell systems were used for assay, the amount of interferon was adjusted to give 50% depression of virus RNA synthesis in those cells. Anti-interferon activity is shown by an increase in the level of $^3$H-uridine incorporation (due to virus RNA synthesis) above that due to interferon alone. Subsequently, an IIP assay was developed, in which dilutions of supernatant fluid, mouse ascites fluid or IgG n PBS (10 μl) were incubated with about 720 units HuIFN-α(10 μl) at 37° C. for 5 h. Antigen-antibody complexes were then precipitated by the addition of 5 μl normal mouse serum as carrier, followed by 75 μl of sheep mouse immunoglobulin antiserum (slight antibody excess). After incubation at 37° C. for 30 min and at 4° C. for 16 h, the samples were centrifuged at 8000 g for 5 min to remove the antibody-antigen precipitate, and the supernatant was assayed for its residual interferon content by the INAS method in HFF cells.

Anti-interferon activity was initially screened by using the direct method. The test system was first checked for its ability to detect small amounts of anti-interferon by assaying a series of coded samples which were supernatants from other cell fusions, using spleen cells from mice injected with irrelevant antigens. Alternatively, dilutions of the serum from the mouse used for the fusion were used. The results indicated that the effect of dilutions of up to 1/5000 of the mouse serum could be detected by the increase in H-uridine incorporation. The irrelevant supernatant fluids had a small effect upon the assay, apparently increasing the antiviral effect of the inteferon, possibly because of a non-specific effect on virus RNA synthesis. When the supernatant fluids from the hybrid cells obtained from the mice which had anti-inteferon antibodies were tested, several cultures from both series showed low levels of activity. In the assays from the second series, only one culture (well no. 13) was reproducibly active when culture fluids harvested over a period of 2 weeks were assayed. Even with this culture, the effect was very small, the radioactivity being increased by no more than 3% of the virus controls. Some cultures (e.g. well no. 6) showed a reduction in incorporation of radioactivity below that due to interferon alone, probably due to substances in the medium which non-specifically inhibited virus RNA synthesis. To eliminate this effect, all radioactivity in subsequent assays was expressed as a percentage of the corresponding virus control, i.e. the radio activity after incubation of a mixture of culture fluid and fresh medium rather than a mixture of interferon and fresh medium. When the cells from the cultures which showed low levels of anti-interferon activity were cloned in soft agar, a number of clones were isolated which showed anti-interferon activity. This activity was shown against human interferon-α (leukocyte) when assayed on either human or bovine turbinate cells, and also when virus synthesis was measured by either c.p.e., yield or plaque formation as well as by the routine INAS method. The culture fluids had no effect on virus yield in mouse or rat cells or on the effect of mouse or rat interferon in the homologous cells. However, the majority of the clones showing this apparent anti-interferon activity did not secrete detectable amounts of IgG and it was concluded that the anti-inteferon effect was not always due to anti-interferon antibody but sometimes to some other unidentified factor. The clones obtained from the first fusion were abandoned since none of the clones which showed anti-interferon actually released IgG, and while the same effect was shown by clones obtained from the second fusion, use of the reverse plaque assay to test for the presence of secreted mouse immunoglobulin made it possible to identify those clones secreting immunoglobulin. In this way, a clone from well 13, clone 35, subclone 6 (clone 13.35.6) referred to as NK2, was isolated. The NK2 cells were incubated in medium containing C-lysine, and the culture supernatant analysed by SDS-polyacrylamide gel electrophoresis. The autoradiograph of the dried gel indicated that the major product of NK2 cells was an immunoglobulin whose heavy chain had the mobility of a γ-chain and whose light chain had a mobility slightly greater than that of X63 light chain. No trace of the X63 light chain produced by the NS1 myeloma parent was detected in the NK2 supernatant.

The cells of well 13 from the second fusion were cloned twice to yield a clone secreting anti-interferon activity. This activity was also shown by the IgG secreted by the clone, and was readily detected by the IIP anti-inteferon assay. When the extent of neutralization, measured as percentage of the added interferon that remained in the supernatant fluid, was plotted against the immunoglobulin concentration the neutralization curve was very similar to that obtained by the direct interferon assay. The indirect test was apparently more satisfactory than the direct procedure because higher concentrations of immunoglobulin could be used in the smaller volumes employed, and so the test was more sensitive. In addition, in the indirect test, the amount of interferon remaining in the supernatant fluid was titrated directly and the extent of neutralization was estimated by comparing the dilutions giving 50% inhibition of virus RNA synthesis. However, in the direct test, the effect of neutralization was to increase the amount of virus RNA synthesis through movement up the sigmoidal dose-response curve where, at the extremes, a large difference in interferon titre gives only a small difference in the amount of virus RNA synthesis. Thus, the indirect assay involved determining the titre of an interferon preparation, using five dilutions at 0.5 log intervals assayed in duplicate, while the direct assay involved a duplicate assay at one dilution only; it is apparent that the first procedure is inevitably more accurate.

Anti-interferon antibodies have shown to be useful in the characterization of different interferons and the purification of both mouse and human interferons. Their use, however, has been limited by the fact that until recently only impure interferon preparations were available for immunization of animals, and the antisera thus obtained were directed mainly against contaminants in the interferon preparations. Now that leukocyte and lymphoblastoid interferons have been purified to homogeneity, the purified interferon could be used as the immunogen to obtain antisera of higher specificity. However, the existing interferon for immunization of domestic animals required for large-scale production of conventional antiserum. The monoclonal antibody-technique should by-pass these problems, using low amounts of impure interferon to immunize small laboratory animals and, having selected a clone, to produce unlimited amounts of antibody of extremely high specificity and (presumably) high binding capacity. To prepare sufficient IgG for an immunoadsorbent column NK2 cells were injected subcutaneously into BALB/c mice ($10^7$ cells per mouse) and when tumours had developed serum samples were collected and pooled. IgG was purifed from a pool of 18ml of serum by ammonium sulphate precipitation and DEAE-ion exchange chromatography. Purified NK2IgG (14 mg) was coupled to 1 ml of CNBr-activated Sepharose (Pharmacia) and tested as an immunoadsorbent. The results, demonstrate that in a single passage through a 0.5-ml column of NK2-Sepharose, a partially purified preparation of interferon ($1.6 \times 10^6$ U per mg) was purified almost 100-fold further. (The activity and specific activity of the interferon used was as stated by the suppliers and was not independently measured.) Insufficient material was available for accurate determinations of protein concentrations, and so, as an alternative approach to assessing the purity of the interferon after a single passage through the NK2-Sepharose column ("IF-A"), we radiolabelled an aliquot with $^{125}I$ and analysed it by SDS-PAGE.

To show that the material retained on the column (IF-A) had indeed bound specifically to the NK2-Sepharose, we repurified $^{125}I$-IF-A by a second passage through the same column. This time, the 18,000-MW band was specifically retained and eluted from the column, suggesting that at this stage the material was pure. An apparent MW of 17,500 or 18,000 for a leukocyte interferon component has been reported elsewhere.

As a more stringent test of the ability of the NK2-Sepharose to purify lymphoblastoid interferon, a crude sample of extracellular medium from stimulated Namalwa cells was applied to a 0.5-ml column. The results indicate a purification of about 5,000-fold in a single step. We have not investigated the purity of this material by SDS-PAGE but the specfic activity is roughly the same as that of IR-A ($1.2 \times 10^8$ U per mg).

The results described above clearly demonstrate that the monoclonal antibody produced by NK2 is a very useful reagent for human lymphoblastoid interferon purification. Because the antibody is the product of a transplantable tumour and can easily be purified from the serum of tumour-bearing mice, there is no limit to the amount of NK2 antibody that could be made without any further need for interferon as immunogen. Thus, the protocols described here could easily be scaled up for the large-scale purification of interferon. An important advantage of the monoclonal antibody is that this method of purification is equally applicable to interferon from human leukocytes, Escherichia coli or indeed from any other source of human interferon, provided it contains the NK2 antigenic determinant.

Another use of the monoclonal antibody of this invention is in immunoassay of interferon-α. In one such assay, an immunoradiometric assay, a sheep anti-interferon antibody is attached to polystyrene and serves to anchor the interferon present in the sample to the solid phase. The bound interferon is then detected by the addition of $^{125}I$-NK2 (monoclonal anti-Hu-IFNα) and measurement of the counts bound to the solid phase. We have used three forms of polystyrene as the solid phase.

(1) 3 ml test tubes (LP3, Luckham, Ltd., Bungers Hill, U.K.)

(2) 96-well microtiter trays (M24, Gibco Europe, Ltd., Uxbridge U.K.)

(3) 6.5 mm beads (Northumbria Biologicals Ltd., Framlington, U.K.)

In the first case the whole tube was counted to measure the bound $^{125}I$-NK2. When trays were used the bottom of each well was cut off with a hot wire and transformed to a clean tube for counting. In the third case the beads were incubated in 20- or 60-well trays (93-0402, Abbott Laboratories, Basingstoke, U.K.) and transferred to tubes for counting. The incubation volumes used were 1 ml or 0.1 ml (tubes), 0.1 ml (wells) and 0.2 ml (beads). All three supports were found to be satisfactory and for assaying large numbers of samples the beads were preferred for their convenience.

NK2 antibody was purified from the serum and ascites fluid of mice carrying NK2 tumours by ammonium sulphate precipitation and DEAE ion-exchange chromatograph, labelled by the chloramine-T method and desalted on Sephadex G-50 (fine) column. The labelled IgG had a specific activity of about 2 Ci/μmole or about 1 atom $^{125}$I per molecule IgG.

In each assay a standard curve was constructed using either the interferon reference standard MRC 69/19 or a laboratory standard. In one such curve the counts bound at 8,000 U/ml were at a maximum; no further increase was observed with interferon concentrations up to $10^6$ U/ml. The low level of non-specific binding (<1%) of input counts is an important characteristic of the assay.

The assay conditions are as follows.

IgG was purified from a sheep anti-Hu-IFN antiserum (450,000 neutralising units/ml) by ammonium sulphate precipitation and DEAE-cellulose ion exchange chromatography and coated onto polystyrene beads by incubation of the beads at 4° for 16 h in the sheep IgG (20 μg/ml in PBS. 5 mM EDTA, 0.1% NaN$_3$). Several hundred beads were coated, washed in PBS, 10% horse serum (Sera-Lab, Crawley Down, Sussex U.K.). 0.1% NaN$_3$ (HS medium) and stored in HS medium at 4°. Assay trays (20- or 60-well Abbott) were incubated with HS medium at 4° to block any sites for protein attachment. Interferon samples were diluted in HS medium and duplicate samples (200 μl) added to antibody-coated beads (1 bead per well). After 4 h at 4° the beads were washed with 12 ml HS medium each using a combined dispenser/aspirator ("Pentawash", Abbott). After removal of any residual medium, $^{125}$I-NK2 (purified IgG, 40,000 cpm) was added and incubated for 16 h at 4°. The beads were washed as before and transferred to a gamma-counter.

These conditions have been chosen for the convenient measurement of samples encountered in the purification of interferon. Such samples have values of $\sim 10^3$–$10^7$ U/ml and the assay is in routine use in our laboratory to monitor such fractions. Solutions containing $>10^3$ U/ml are diluted by serial dilution and the titration curve obtained matched to the standard curve.

The immunoradiometric assay offers considerable advantages over the conventional biological assays. Since the antibody-coated polystryene can be stored at 4°, samples can be assayed at short notice and the results are obtained within 24 h of beginning the assay. The reproducibility between assays is much better with the immunoradiometric assay. Four measurements of a solution of 2000 U/ml gave a value of 3063±345 cpm in independent assays in which the input cpm ranged from 47,000–53,000 cpm. Only small amounts of sheep antibody are used, since the IgG solution used to coat the polystyrene can be re-used several times without apparently reducing the sensitivity of the assay. The quality of the sheep antibody may not be a critical factor in the success of the assay, and other antibodies to Hu-IFNα could probably substitute equally well. The assay exploits the specificity of the monoclonal antibody NK2 and since this is the product of a hybrid myeloma cell line in culture it can be produced in large amounts without any change in quality. Finally the assay is inexpensive (especially since all the plastic ware except the beads may be re-used), lends itself to automation and several hundred samples can be assayed by one person in a day.

For the measurement of interferon in biological fluids an assay must be capable of detecting much lower levels of interferon than those encountered in production and purification. The results show that at low interferon concentrations the counts bound are proportional to the interferon concentration. It can be seen that concentrations of $\geq 50$ U/ml can be easily measured.

The NK2 antibody is an important advance over antibodies produced by conventional methods. The latter, while strongly neutralizing interferon activity, cpomprise a range of immunoglobulin molecules directed against various antigenic sites on the interferon molecule. They also contain antibodies to the impurities present in the interferon preparations used to immunize the animals, and this has limited their use in interferon purification. The monoclonal antibody, on the other hand, while not showing a high neutralizing titre against the biological activity of interferon, has many advantages because of its specificity and the ease of production of large amounts of antibody in mice injected with the hybrid myeloma.

We claim:

1. A monoclonal antibody produced by a murine derived hybrid cell line wherein the antibody is capable of specifically binding to at least one antigenic determinant of interferon-α.

2. A monoclonal antibody according to claim 1 wherein the antibody is capable of specifically binding to at least one antigenic determinant of human interferon-α.

3. A monoclonal antibody according to claim 1 or 2 wherein the antibody is an immunoglobulin molecule of the type IgG or IgM.

4. A monoclonal antibody according to claim 1 for use in a process for purifying interferon-α.

5. A monoclonal antibody according to claim 1 for use in an immunoadsorbtion purification process for interferon-α.

6. A monoclonal antibody according to claim 1 in an immunoassay for interferon-α.

7. An immunopurification process for extracting interferon-α from a sample containing interferon-α wherein the sample is passed through an immunoabsorbent column comprising a monoclonal antibody according to claim 1 bound to a solid phase support.

* * * * *